(12) United States Patent
Cheong

(10) Patent No.: US 7,132,046 B2
(45) Date of Patent: Nov. 7, 2006

(54) STAINLESS STEEL TUBING/FRIT WITH SINTERED INORGANIC PARTICLE, THE CHROMATOGRAPHY COMPRISING IT, AND THEIR MANUFACTURING METHOD

(75) Inventor: Won Jo Cheong, Keangnam Apt.3-708, Banpodong, Seochogu, Seoul (KR)

(73) Assignees: Won Jo Cheong, Seoul (KR); Kwang Choon Chung, Seoul (KR)

( * ) Notice: Subject to any disclaimer, the term of this patent is extended or adjusted under 35 U.S.C. 154(b) by 182 days.

(21) Appl. No.: 10/490,433

(22) PCT Filed: May 23, 2003

(86) PCT No.: PCT/KR03/01014

§ 371 (c)(1),
(2), (4) Date: Mar. 24, 2004

(87) PCT Pub. No.: WO03/101608

PCT Pub. Date: Dec. 11, 2003

(65) Prior Publication Data

US 2004/0238447 A1    Dec. 2, 2004

(30) Foreign Application Priority Data

Jun. 3, 2002    (KR) ..................... 10-2002-0031123

(51) Int. Cl.
*B01D 15/08* (2006.01)

(52) U.S. Cl. ............................. 210/198.2; 210/510.1; 210/656

(58) Field of Classification Search ............... 210/635, 210/656, 659, 198.2, 510.1
See application file for complete search history.

(56) References Cited

U.S. PATENT DOCUMENTS 4,475,821 A * 10/1984 Koch et al. .............. 366/160.1

(Continued)

FOREIGN PATENT DOCUMENTS

JP    60-166262 A    8/1985

(Continued)

OTHER PUBLICATIONS

PTO Translation 2006-1004 of Japan Patent No. 60-166262, pp. 1-7.*

(Continued)

*Primary Examiner*—Ernest G. Therkorn
(74) *Attorney, Agent, or Firm*—Birch Stewart Kolasch & Birch, LLP

(57) ABSTRACT

This invention is about metal tubing/frit applicable in liquid chromatography and a chromatography column manufactured by using the same. In detail, this invention is about manufacturing the metal tubing/frit by treating a powdered inorganic oxide such as silica, alumina, zirconia, and titania with a strong base, drying it with some humidity included, scrubbing it into powders, putting it in the tip of a chromatographic metal tubing at a proper depth, and by sintering the powders to form a durable sintered frit on the inner wall.

This invention is also about a liquid chromatographic column manufactured by installing the metal tubing/frit's with a sintered end frit at the column inlet and outlet unions and by placing the cylinder-like column main body tubing packed with a stationary phase between the unions.

The metal tubing/frit manufactured according to the description above is not placed inside the column as in the conventional column design, thus it is easily replaced and fixed without disassembling the column, and the column of this design can displace the conventional microcolumn of complicated production process and high cost.

4 Claims, 7 Drawing Sheets

U.S. PATENT DOCUMENTS

| | | | |
|---|---|---|---|
| 4,476,017 A * | 10/1984 | Scharff et al. | 210/94 |
| 4,759,916 A * | 7/1988 | Heikel | 423/71 |
| 4,806,238 A * | 2/1989 | Sattler et al. | 210/198.2 |
| 5,348,658 A * | 9/1994 | Fuchs et al. | 210/656 |
| 5,453,163 A * | 9/1995 | Yan | 204/451 |
| 5,582,723 A * | 12/1996 | Boone et al. | 210/198.2 |
| 5,651,885 A * | 7/1997 | Schick | 210/198.2 |
| 5,730,943 A * | 3/1998 | Ford et al. | 422/101 |
| 5,985,140 A * | 11/1999 | Dewaele | 210/198.2 |
| 6,068,767 A * | 5/2000 | Garguilo et al. | 210/198.2 |
| 6,095,572 A * | 8/2000 | Ford et al. | 285/361 |
| 6,136,187 A * | 10/2000 | Zare et al. | 210/198.2 |
| 6,221,252 B1 * | 4/2001 | Hargro et al. | 210/656 |
| 6,224,775 B1 * | 5/2001 | Foley et al. | 210/635 |
| 6,344,145 B1 * | 2/2002 | Garguilo et al. | 210/635 |
| 6,395,183 B1 * | 5/2002 | Valaskovic et al. | 210/656 |
| 6,527,951 B1 * | 3/2003 | Tuvim | 210/198.2 |
| 6,579,459 B1 * | 6/2003 | Gjerde et al. | 210/635 |
| 6,679,989 B1 * | 1/2004 | Willis et al. | 210/198.2 |
| 6,780,325 B1 * | 8/2004 | Murata et al. | 210/656 |
| 2005/0000875 A1 * | 1/2005 | Murata et al. | 210/198.2 |
| 2005/0077222 A1 * | 4/2005 | Dawes et al. | 210/198.2 |

FOREIGN PATENT DOCUMENTS

JP      P2000-088805 A      3/2000

OTHER PUBLICATIONS

Machine Translation of Japan Patent No. 2000-88805A, pp. 1-47.*
PTO Translation 2006-1613 of Japan Patent No. 2000-88805A, pp. 1-36.*

* cited by examiner

STAINLESS STEEL TUBING/FRIT WITH SINTERED INORGANIC PARTICLE, THE CHROMATOGRAPHY COMPRISING IT, AND THEIR MANUFACTURING METHOD

REFERENCE TO RELATED APPLICATIONS

This application is a 371 of PCT/KR03/01014 filed May 23, 2003.

TECHNICAL FIELD

This invention is about metal tubing/frit's and columns manufactured by using the same for liquid chromatography. First, this invention is about powders with tiny amount of humidity manufactured by treating inorganic oxide powders such as silica, alumina, titania, and zirconia with a strong base followed by drying.

This invention is also about manufacturing metal tubing/frit's by putting the above mentioned powders into the tip of metal tubing designed for column chromatography at a proper height and by sintering them into a solid frit.

This invention is also about a liquid chromatographic column manufactured by installing the above mentioned metal tubing/frit's with a sintered end frit at the column inlet and outlet unions and by placing the cylinder-like column main body tubing packed with a stationary phase between the unions.

BACKGROUND ART

The liquid chromatography column is composed of three major parts, that is, a column body tubing, end-fitting blocks at both ends of the column body, and a filler as a static phase(stationary phase) packed in the column.

The column body tubing is made of various material such as stainless steel, glass-lined stainless steel, polymer, and polymer coated silica, etc.

Porous powders are usually used as stationary phases. Porous silica, alumina, zirconia, and their ligand-attached or polymer-coated products are usually used, and various kinds of porous block copolymer powders are also used. The most typical stationary phase at present is porous octadecyl ligand attached silica, $C_{18}$.

Porous disc-type frits are placed in both ends of a column to keep the stationary phase in and to let the mobile phase penetrate in common columns although they are different in shapes. Such frits are treated very carefully since frits directly influence chromatographic resolution, and various researches for frits have been being carried out.

The monolith column has been recently proposed. The whole stationary phase of the monolith column is one body with numerous multiple porous channels, thus it does not need any frit (Svec et al., Anal. Chem. 1992, 64, 820–822; Minakuchi et al., Anal. Chem., 1996, 68, 3498–3501).

Various types of column end fittings and frit installation mechanisms are illustrated in the "Handbook of HPLC" (1994, GIT-Verlag) edited by Unger. In all cases, frits are installed inside the column main body, and the frits cannot be removed without disassembling the column.

Additional various designs of frits and end fittings have been proposed. For example, polymer encased stainless steel disc frits were used in the U.S. Pat. No. 4,399,032(1983), and trapezoidal disc type frits, in the U.S. Pat. No. 4,966,696(1990). Such frits were used to minimize anomalous perturbation of mobile phase flow and consequent column efficiency degradation owing to differences among the inside diameter of column, the diameter of porous frit disc, and the inside diameter of connecting tubing. Another special design is given in the U.S. Pat. No. 5,227,059(1993) where a tough and flexible polymer insert with a central flow channel was proposed to be installed in front of the column inlet frit in order to remove any void volume owing to prolonged use of the column and consequent partial collapse of the stationary phase by just tightening the insert.

Hernan Cortes et al proposed to prepare an unreplaceable porous ceramic plug frit at the column end by putting a potassium silicate solution into the end of the column main body and by causing sintering on vapor heating in the U.S. Pat. No. 4,793,920(1988). This method was also used in production of microcolumns in the U.S. Pat. No. 5,679,255 (1997), and only the treatment of column outlet was mentioned, in particular, but not the treatment of column inlet, which leads us to guess that the conventional separate frit technique was used for the inlet side.

The technique of making fixed frits in the column main body tubing is generally used in production of microcolumns, especially microcolumns made of polymer coated silica capillary.

The initial microcolumn frit designs were, however, non-porous and imperfect, and a metal wire whose diameter was slightly smaller than the inside diameter of the silica capillary, or another silica capillary with very narrow I.D. whose O.D. was slightly smaller than the I.D. of column capillary, was used in the U.S. Pat. No. 4,483,773(1984). In addition, a silica capillary column encased in soft polymer tubing was proposed in the U.S. Pat. No. 5,938,919(1999) where the conventional replaceable frits were used.

The recent trend of silica capillary microcolumns is shifting swiftly toward monolithic columns where the whole column functions as a large frit, too. Details of monolith columns have been introduced in some review articles (Vissers et al., J. Chromatogr. A, 1999, 856, 117–143; Jinno et al., Trends in Analytical Chemistry, 2000, 19, 664–675; Bartle et al, J. Chromatogr. A, 2000, 892, 279–290), and patents of various monolith columns have appeared.

For example, the method of preparing fixed frits at both ends of the column by partial heat treatment of a packed silica capillary was introduced in the literature (Boughflower et al, Chromatographia, 1995, 40, 329; Smith et al, Chromatogrphia, 1994, 38, 649). A research group made use of such concept, and packed a silica capillary with porous stationary phase powders, and sintered the whole stationary phase by heating with a ring-type electric heating wire, leaving the whole stationary phase combined but the porous spherical structures of the powders unchanged, in the U.S. Pat. No. 5,858,241(1999). A monolith column was proposed to be prepared by putting the dispersed solution of stationary phase powders, water, a solvent such as alcohols, and a metal alkoxide by a syringe in a silica capillary, and by applying heat treatment and vacuum in the U.S. Pat. No. 6,136,187(2000).

The conventional arts of preparing frits of liquid chromatography columns described above can be categorized into two techniques.

The first one is to place separate frits. In this case, the frit is exclusively installed inside the column end-fitting, thus, if the frit is clogged and needs to be replaced, the column end-fitting should be disassembled. Besides, perturbation of mobile phase flow and consequent reduction of column efficiency can occur if the frit diameter is very larger than the column I.D. or the I.D. of connection tubing. Adopting complicated designs for the frit structure to solve such problems yields cost increase and inconvenience of use.

Furthermore, it is very difficult to make separate miniaturized frits for microcolumns with I.D. of 0.5 mm or less whose relative importance has been rapidly increased, and, actually, microcolumns with such frits are not commercially available.

The other frit technique is to make permanent frits at the column ends or for the whole column without using separate frits. In this case, column repacking is impossible, and the column lifetime ends when the frit is clogged or a crack or void volume develops in the column. First, in the case of permanent end frits only at the column inlet and outlet, cracks in the packing structure are sometimes observed after formation of end frits, and the column efficiency is degraded. Furthermore, if frit clogging happens in the course of forming the inlet frit after packing the column with the stationary phase powders, then the whole column finishes its lifetime without being used at all.

The monolith column in which the whole stationary phase is one porous phase and a huge frit as well, has raised a lot of interest, and has its own advantages and disadvantages. First of all, it is difficult to make a monolith without a void volume in a rigid conventional stainless steel column with I.D. of 1–5 mm, thus formation of monolith is confined in a heat-shrinkable polymer tubing. Such manufacturing technique seems to suffer from low reproducibility of production. A lot of care should be taken in end fitting treatment of the polymer tubing of low strength, and such products will have endurance problem. It is relatively easy to make silica capillary monolith column with I.D. of 0.5 mm or less, but lots of high level man-power and time are required for preparation of monolith reactants, formation of monolith, and cleaning the monolith. Furthermore, production reproducibility of silica capillary monoliths is not well known, and it is improper to apply to a pilot or industrial scale.

There has been no frit technique so far to make permanent frits not in the column main body but in the connection tubing between the column and other devices such as an injector or detector. If such a frit technique is avaliable, the structure of column end fitting becomes simple, and it is possible to make useful columns at lower prices by using commercial unions without a new special design. The problem of column efficiency reduction owing to a larger frit diameter compared to the column I.D. is eliminated for this tubing/frit design, and the tubing/frit can be easily replaced without disassembling the main column body when the frit is clogged. The problem is, however, it is difficult to make a permanent frit combined to the inner surface of the connection tubing end with endurance over high pressure and mobile phase flow on packing or operating the column.

The inventor studied repeatedly on production of tubing/frit and column of simple design, convenience, and low cost, and developed the method of producing a durable frit/tubing by sintering porous inorganic particles chemically and thermally at the tip of metal connection tubing, and the method of producing a column of a new simple design by installing the frit/tubing at the column outlet union followed by packing the column with a proper stationary phase and finally installing the column inlet union with the frit/tubing of chemically and thermally sintered frit.

DISCLOSURE OF INVENTION

The purpose of this invention is to offer a tubing/frit and a chromatographic column installed with the tubing/frit's with the advantages of simple design convenience of column production, and low cost.

The purpose of this invention is also to offer a tubing/frit of endurance over mobile phase flow and high pressure.

The purpose of this invention is also to offer the method of producing inorganic powders to make the above tubing/frit.

The purpose of this invention is also to offer a tubing/frit with a sintered solid frit made of inorganic oxide powders formed on the inner wall of the tubing.

The purpose of this invention is also to offer a chromatographic column that can be reused by replacing the connection tubing without disassembling the column when frit replacement is necessary.

This invention is about metal tubing/frit's and chromatographic columns with them, and this invention offers the production method of inorganic oxide powders for chromatographic frits obtained by treating inorganic oxides such as silica, alumina, titania, and zirconia, in detail, followed by drying to a product with some humidity.

This invention also offers the production method of metal tubing/frit's made by filling the above powders in a tip of metal tubing at a proper height followed by forming a solid sintered frit on the inside wall of the tubing.

This invention also offers the production method of chromatography columns made by connecting the tubing/frit with a sintered powder frit at the end of the tubing produced by the above process to a union followed by placing a cylindrical column main body tubing packed with a stationary phase between two such unions.

The more detailed description of this invention follows below.

The inorganic oxide powders of this invention for frits are produced by treating an inorganic oxide by a strong base followed by drying at room temperature or at 50–80° C. to give a product of some latent humidity.

The above powders can be any inorganic powders, and silica, zirconia, alumina, and titania are included for example, silica being the preferred one. The particle sizes are 1–20 μm, and the pore size, less than 500 Å, depending upon some factors such as targeted compound.

The types of strong bases are not confined, either, in this invention, and include all the hydroxides and carbonates of alkali and alkali earth metals such as KOH, NaOH, for example, with NaOH being the preferred one. The base is used at the concentration of 3~10 weight % in the ratio of 1~20 mL per gram of inorganic oxide powders.

The inorganic oxide powders obtained by the above method are allowed to be dried to include microcrystalline base powders and some humidity, and show the trend of maintaining the spherical structure with largely decreased porosity. Examining the microstructure of the above inorganic oxides in detail by the SEM photograph of FIG. 4, we find that the inorganic oxide powders(silica), in general, maintain the spherical shape, some of them being partially fused together. We also observe that microcrystalline base particles are mixed with the inorganic oxide powders.

To make a frit using the above inorganic oxide powders with some latent humidity, first a metal tubing is filled with the inorganic oxide powders in the bottom part of the tubing at a proper height, and is placed in an electric furnace and heated for 3~6 hours at 400~1,000° C.

A durable sintered frit is produced since the inorganic oxide powders are attached to the tubing inner wall by the sintering process, and the frit can endure mobile phase flow and high operation pressure owing to the strong bonds formed by sintering.

The content of the inorganic oxide powders filled varies depending upon the dimension of metal tubing, and the height can be adjusted by the content. For example, in the experiments of this invention, the height of filled inorganic oxide powders was 0.3~5 mm for tubing of 4~10 cm length, 0.1~0.8 mm I.D., and 1.6 mm O.D.

An additional chemical treatment can be carried out upon the above tubing/frit in order to increase chemical stability and deactivate the surface hydroxyl group. In detail, the stabilized tubing/frit can be obtained by putting the tubing/frit and a silylation agent in a $C_6$~$C_8$ hydrocarbon solvent followed by heating for 1~5 hours, preferably 3 hours or more, at 60~100° C.

Sintered frits of this invention can also be made by other methods beside the above mentioned method. They are made by putting porous inorganic powders in the tip of the tubing and soaking the tip with water or a basic solution followed by sintering at 500–800° C. The sintered frits are obtained by such a method, but, in this case, the frit tends to be a little weaker owing to the release of packing structure of the powders upon absorbing a liquid. Nonetheless, such a method can also yield a sintered tubing/frit strong enough to be applied to chromatographic columns.

According to FIG. 5a of the sintered silica powders on the inner surface of metal tubing, the surface of metal tubing is uneven, and such high unevenness allows attachment of the sintered frit to the inner wall of metal tubing. The same trend is observed in FIG. 5b, too. Actually, we found that the tubing/frit's were not destroyed in a high pressure fluid flow.

The inventor proposes a chromatographic column of a new structure using the tubing/frit prepared by the process above.

As shown in FIG. 1, in the chromatographic column of this invention, the tubing/frit(101a) with a sintered frit(10a) formed at a tubing end, is connected to the inlet of the main body column tubing(100) packed with a stationary phase (20) through connecting means(102a,103a,103a',104a, 104a'), and the outlet of the main body column tubing(100) is also connected to the tubing/frit(101b) with a sintered frit(10b) formed at a tubing end through connecting means (102b,103b,103b',104b,104b'), and the sintered frits(10a, 10b) face each other with the main body column tubing inside.

In order to make the above chromatography column, where the tubing/frit's(101a,101b) with sintered frits(10a, 10b) are connected to the cylindrical main body column tubing(100) packed with a stationary phase(20), and the components are combined by the common connecting means so that the frits(10a,10b) at the column inlet and outlet face each other, the metal tubing/frit(101b) with a sintered frit(10b) is connected to the main body column tubing(100) by installing the tubing/frit(101b) at the column outlet union(102b), and the column outlet part is formed by installing it at the union(102b) with nuts(103b,103b') and ferrules(104b,104b') as connecting means, and the other side of the main body column tubing(100) is connected to the column packing apparatus, and the main body column tubing(100) is packed with a stationary phase (20), and the metal tubing/frit(101a) with a sintered frit(10a) is connected to the other side of the main body column tubing(100) by installing it at the column inlet union(102a), and the column inlet part is formed by using nuts(103a, 103a') and ferrules(104a,104a') as connecting means.

As the column outlet part is examined in detail as shown in the expanded figure(FIG. 2a), the tubing/frit(101b) with a sintered frit(10b) is installed at the column outlet union (102b) with a nut(103b') and a ferrule(104b) as connecting means. The main body column tubing(100) to be packed with a stationary phase(20) later, is connected to the other side of the union(102b) with a nut(103b) and a ferrule (104b'), and the other side of the main body column tubing (100) is connected to the column packing apparatus.

The outside diameter of the above connecting tubing (101a,101b) is 1.6 mm or less, and their inside diameter is variably adjusted to be 0.1, 0.125, 0.25, or 0.5 mm, etc., depending upon the column size. Any metallic material such as stainless steel, nickel, copper, or alloys can be used for the tubing, but stainless steel of less corrosion is preferred. The tubing length should be minimized, but should be enough for fitting, and is adjusted to be 4~10 cm.

The above tubing frit(101b) can be coupled to a detecting device through an independent union, which will be explained later. In the chromatography column of this invention, the separate frits in a convention column are not installed, and even the central hole of the union that is vacant in a conventional column is filled with the stationary phase (20) to yield an advantage of eliminating the void volume.

The inlet part of the chromatography column is shown in FIG. 2b as an expanded view, and is processed in the same fashion as the outlet part. In detail, The metal tubing/frit (101a) with chemically and thermally sintered frit(10a) is installed at the column inlet union(102a) with a nut(103a) and a ferrule(104a), and the other side of the union is connected to the main body column tubing(100) with a nut(103a') and a ferrule(104a'). The other side of the above tubing/frit(101a) is connected to a guard column or to a sample injector.

The above nuts, ferrules, and unions are well known in this area, and can be easily purchased depending upon the column size among commercially available products.

For example, outside diameters(O.D.) of common main body column tubing(100) are classified as 1.6, 3.2, 6.4, 9.6 mm, etc., depending upon the inside diameters(I.D.). A symmetric union is used when the O.D. of the main body column tubing is equal to the O.D. of the tubing/frit, while an asymmetric union is used when the O.D. of the main body column tubing(100) is larger than the O.D. of the tubing/frit.

All the available metals/alloys such as stainless steel, nickel, copper, etc., and polymer materials can be used for the main body column tubing(100), but stainless steel of less corrosion is preferred although this invention is not confined to specific materials. Stainless steel tubing with a mirror-like ground inner wall or stainless steel tubing with a glass-lined inner wall can be used among the above stainless steel tubings. Stainless steel tubing with a mirror-like inner wall is recommended when the I.D. is equal to or larger than 1 mm, and glass-lined stainless steel tubing is recommended when the I.D. is less than 1 mm.

Packing the column with a stationary phase(20) is done by a common method, thus, for example, a stationary phase(20) is dispersed in a proper polar or nonploar solvent such as methanol, acetone, or hexane, depending upon the type, and the slurry is ultrasonicated, poured into a slurry reservoir of 1~40 mL depending upon the column size, then column packing is executed immediately. The column is rapidly packed for 2~10 min. under a high pressure of 10,000~14, 000 psi.

After packing the stationary phase(20), the main body column tubing(100) is detached from the slurry packing apparatus, and is connected to the column inlet union installed with the tubing/frit(101a) with a chemically and thermally sintered powder frit(10a) as in FIG. 1 to complete the column.

In the chromatography column of this invention installed with a tubing/frit with sintered powder frit, the frits are not installed inside the column as in the convention column, but installed in the connecting tubing, and therefore there is an advantage that only the connecting tubing is replaced without disassembling the column when it is necessary to replace the frit.

In detail, in order to save the cost when replacing the tubing/frit, a one-body polymer nut/ferrule can be used instead of a separate stainless steel nut and a ferrule when the tubing/frit's(101a, 101b) are installed as in FIGS. 2a and 2b, thus only the tubing/frit is replaced and the polymer nut/ferrule is reused.

Especially, the new column structure of this invention is advantageous in the area of microcolumn whose inside diameter is 0.5 mm or less.

The packed silica capillary column is at present the only commercially available microcolumn with an I.D. of 0.5 mm or less, but in this column, the frit is made to be permanently combined to the column end, and the production cost is high owing to the complicated process, and furthermore there is a critical disadvantage that the column finishes its lifetime when the frit is clogged since the frit cannot be replaced. On the other hand, in the column structure of this invention, frit replacement is easy and the column can be fixed by disassembling if necessary.

The chromatography column of this invention can be connected to a detecting device such as a mass spectrometer via a separate union. In a desirable embodiment as shown in FIG. 3, a commercially available asymmetric union(202) is connected to the column of this invention, and the ferrule (204) of the small side of the union is replaced by a commercial Vespel/graphite ferrule(204). Then, a capillary (200) that can be directly connected to the detector interface, for example, a polymer reinforced silica capillary (200) is cut in a suitable length, and coupled. The connecting means of the column outlet side of the asymmetric union are the pre-described ferrule(104c) and nut(103c).

The connection to the detecting device is not confined to a mass spectrometer, and other detecting device can be coupled via connecting means(union 202, nut 203, ferrule 204).

Figure 1:
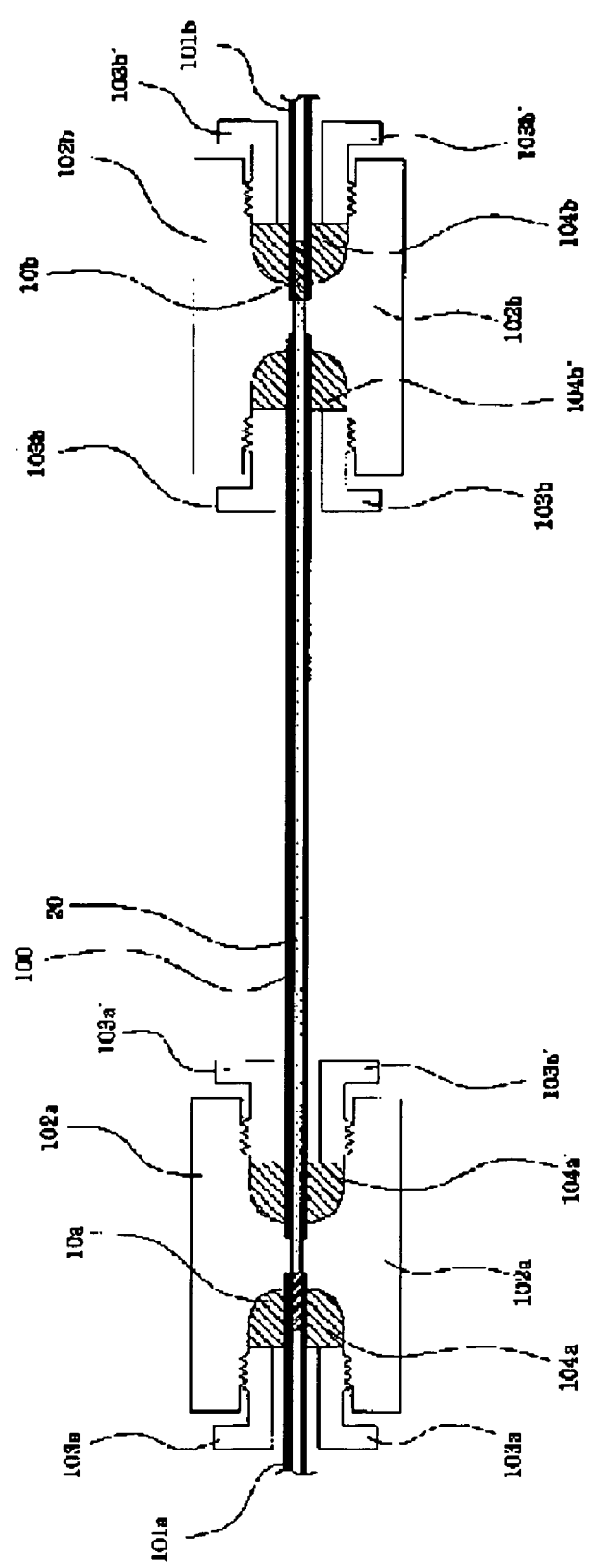
FIG. 1 is the cross section of the liquid chromatographic column with metal tubing/frit's manufactured by this invention.

DESCRIPTION OF CODE FOR THE MAJOR PARTS OF DRAWINGS 10a, 10b: sintered frit
20: stationary phase
100: column main body tubing
101a, 101b: metal tubing of the column inlet and outlet
102a: column inlet union
102b: column outlet union
103a, 103a', 103b, 103b', 103c, 203: nuts
104a, 104a', 104b, 104b', 104c, 204: ferrules
200: capillary
202: asymmetric union

BEST MODE FOR CARRYING OUT THE INVENTION

The detailed embodiments of this invention are given below. However, those are just some examples of this invention, and this invention is not to be limited to the illustrative embodiments set forth herein.

EXAMPLE 1

Production of Metal Tubing/Frit's with Chemically and Thermally Sintered Silica Frits I: 0.1 mm I.D.

Figure 4:
FIG. 4 is the micro structure SEM (scanning electron microscope) photograph of the silica powders which were treated with a strong basic solution and dried

One gram spherical porous 5μ, 60 A° silica particles are dispersed in a 5 mL 10 wt % NaOH solution, and the dispersion is spread over a hard and flat polymer surface as a thin layer, and dried at room temperature under a glass board to protect the dispersion layer from falling dirts. The dried layer is scraped with a polymer scoop and rubbed gently with a round pestle into fine powders. In the microstructure of the above powders observed by a scanning electron microscope (FIG. 4), most of the powders maintain their spherical shapes, and they are partially fused and mixed with minute needle crystals of NaOH. The powders are then uniformly spread on a flat polymer surface with a depth of 2 mm or so. Metal tubings of 5 cm×0.1 mm×1.6 mm (length×I.D. ×O.D.) are located vertically over the fine powders, and are allowed to hit the surface gently and at various spots 50 times to get the particles in with a depth of 2 mm. The outer wall of the tubing is cleaned with a soft tissue.

The tubing with the silica powders filled at the tip is placed in an electric furnace and heated at 500° C. for 5 hours under nitrogen atmosphere to yield a tubing/frit with a sintered silica frit.

Figure 5A:
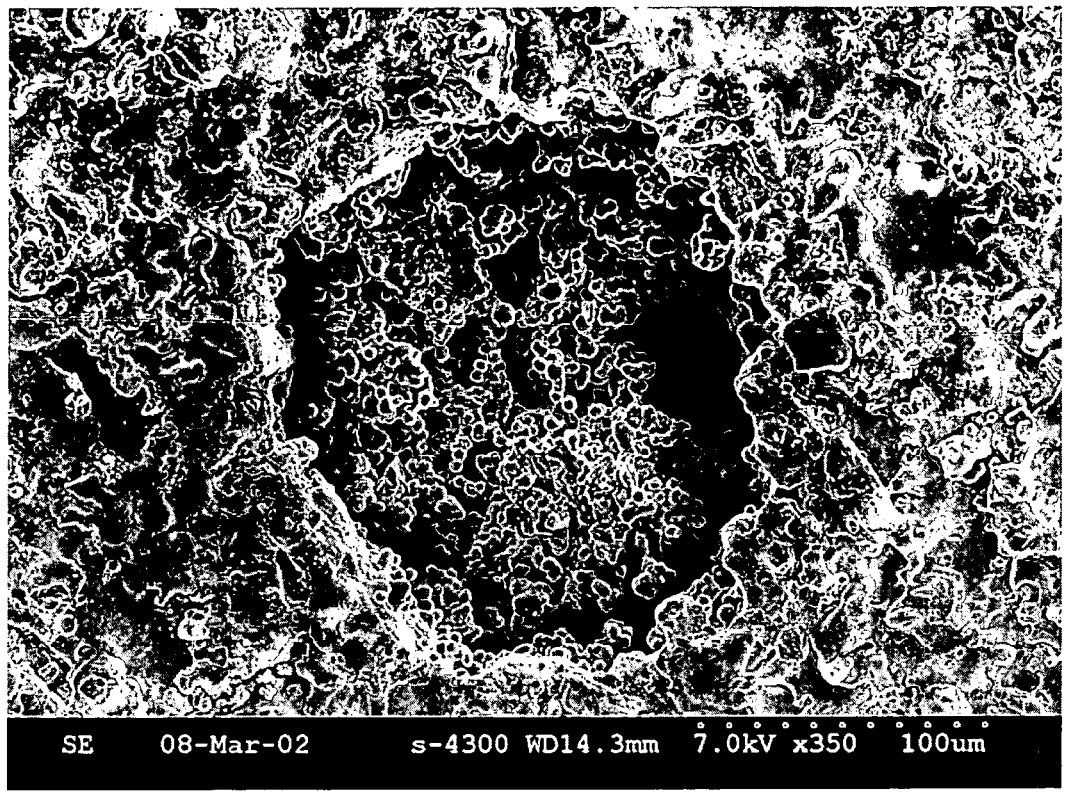
FIG. 5a and FIG. 5b are the micro structure photographs showing sintered frits in the metal tubing.

According to FIG. 5a of the cross-section of the above tubing/frit, the silica particles are fused one another, and attached to the inner wall of the stainless steel tubing to give a durable sintered silica frit.

The frit made in this embodiment is strong enough to sustain when a high pressure of 8,000 psi is rapidly applied to the tubing/frit. It has such an excellent permeability that a pressure of only 30~50 psi is developed when the tubing/frit is connected to a LC pump and a flow of 2 mL/min is applied.

EXAMPLE 2

Production of Metal Tubing/Frit's with Chemically and Thermally Sintered Silica Frits II: 0.8 mm I.D.

One gram spherical porous 10μ, 100 A° silica particles are dispersed in a 20 mL 5 wt % KOH solution, and the dispersion is spread over a hard and flat polymer surface as a thin layer, and dried at 50–60° C. under a glass board to protect the dispersion layer from falling dirts. The dried layer is scraped with a polymer scoop and rubbed gently with a round pestle into fine powders.

The above silica powders are then uniformly spread on a flat polymer surface with a depth of 2 mm or so. Metal tubings of 5 cm×0.8 mm×1.6 mm (length×I.D.×O.D.) are located vertically over the fine powders, and are allowed to hit the surface gently and at various spots 100 times to get the particles in with a depth of 2~3 mm. The outer wall of the tubing is cleaned with a soft tissue.

The tubing with the silica powders filled at the tip is placed in an electric furnace and heated at 600° C. for 4 hours under nitrogen atmosphere to yield a sintered silica frit.

Figure 5B:
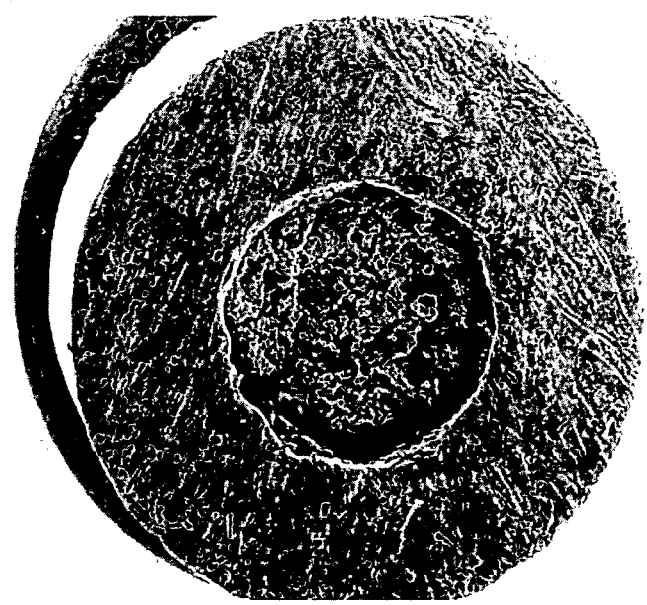

The obtained silica frit is very firm, and according to FIG. 5b of the magnified cross-section of the above tubing/frit, the fused silica particles are well attached to the inner wall of the stainless steel tubing as is observed in FIG. 5a.

The frit made in this embodiment is strong enough to sustain when a high pressure of 8,000 psi is rapidly applied to the tubing/frit., and it has such an excellent permeability that a pressure of only 10 psi is developed when the tubing/frit is connected to a LC pump and a flow of 10 mL/min is applied.

EXAMPLE 3

Production of Metal Tubing/Frit's with Chemically and Thermally Sintered Silica Frits III: 0.25 mm I.D.

One gram spherical porous 5μ, 100 A° silica particles are dispersed in a 10 mL 10 wt % NaOH solution, and the dispersion is spread over a hard and flat polymer surface as a thin layer, and dried at room temperature under a glass board to protect the dispersion layer from falling dirts. The dried layer is scraped with a polymer scoop and rubbed gently with a round pestle into fine powders.

The above silica powders are then uniformly spread on a flat polymer surface with a depth of 2 mm or so, and metal tubings of 5 cm×0.25 mm×1.6 mm (length×I.D.×O.D.) are located vertically over the fine powders, and are allowed to hit the surface gently and at various spots 100 times to get the particles in with a depth of 2~3 mm. The outer wall of the tubing is cleaned with a soft tissue.

The tubing with the silica powders filled at the tip is placed in an electric furnace and heated at 500° C. for 5 hours under nitrogen atmosphere to yield a sintered silica frit.

The frit made in this embodiment is strong enough to sustain when a high pressure of 8,000 psi is rapidly applied to the tubing/frit., and it has such an excellent permeability that a pressure of only 10~20 psi is developed when the tubing/frit is connected to a LC pump and a flow of 5 mL/min is applied.

EXAMPLE 4

Production of Metal Tubing/Frit's with Sintered Alumina Frits.

One gram spherical porous 5μ, alumina particles with a specific surface area of 70 m²/g are dispersed in a 5 mL 10 wt % NaOH solution, and the dispersion is spread over a hard and flat polymer surface as a thin layer, and dried at room temperature under a glass board to protect the dispersion layer from falling dirts. The dried layer is scraped with a polymer scoop and rubbed gently with a round pestle into fine powders.

The above alumina powders are then uniformly spread on a flat polymer surface with a depth of 2 mm or so, and stainless steel tubings of 5 cm×0.25 mm×1.6 mm (length×I.D.×O.D.) are located vertically over the fine powders, and are allowed to hit the surface gently and at various spots 100 times to get the alumina powders in with a depth of 2~3 mm. The outer wall of the tubing is cleaned with a soft tissue.

The tubing with the alumina powders filled at the tip is placed in an electric furnace and heated at 800° C. for 5 hours under nitrogen atmosphere to yield a sintered alumina frit.

EXAMPLE 5

Production of Metal Tubing/Frit's with Sintered Zirconia Frits.

One gram spherical porous 3μ, 300 A° zirconia particles are dispersed in a 10 mL 5 wt % NaOH solution, and the dispersion is spread over a hard and flat polymer surface as a thin layer, and dried at room temperature under a glass board to protect the dispersion layer from falling dirts. The dried layer is scraped with a polymer scoop and rubbed gently with a round pestle into fine powders.

The above zirconia powders are then uniformly spread on a flat polymer surface with a depth of 2 mm or so, and stainless steel tubings of 5 cm×0.25 mm×1.6 mm (length×I.D.×O.D.) are located vertically over the fine powders, and are allowed to hit the surface gently and at various spots 100 times to get the alumina powders in with a depth of 2~3 mm. The outer wall of the tubing is cleaned with a soft tissue.

The tubing with the zirconia powders filled at the tip is placed in an electric furnace and heated at 900° C. for 5 hours under nitrogen atmosphere to yield a sintered zirconia frit.

EXAMPLE 6

Silylation of the Tubing/Frit

In order to increase chemical stability of the frit/tubing and to deactivate the surface silanol groups, the tubing/frit is treated as follows.

50 Tubing/frit's are placed in a 250 mL flat bottom flask together with 100 mL hexane and 2 mL trimethylchlorosilane, and the mixture was reacted at the reflux temperature for 24 hours. The silylated tubing/frit's are taken out and washed with acetone, water, and methanol in series.

The pyridine adsorption-retention properties of the deactivated sintered silica tubing/frit prepared by the above process, the untreated sintered silica tubing/frit, and the plain stainless steel tubing (all with 0.1 mm I.D. and 5 cm length) are measured and compared.

Each tubing is connected between a 0.5 μL Valco injector and an Isco micro UV detector, and a 0.001 M pyridine solution (solvent:methanol) is injected with 100% methanol as the eluent at a flow rate of 0.005 mL/min, and the chromatograms, retention times, peak heights and bandwidths are measured and compared, the results being given in Table 1.

TABLE 1

Comparison of pyridine retention properties of plain tubing, tubing/frit, and silylated tubing/frit

| tubing | retention time (min) | peak height (mV) | peak bandwidth at half height (min) |
|---|---|---|---|
| plain | 0.514 ± 0.011 | 6.788 ± 0.227 | 1.001 ± 0.031 |
| tubing/frit | 0.495 ± 0.022 | 6.386 ± 0.207 | 1.182 ± 0.092 |

TABLE 1-continued

Comparison of pyridine retention properties of plain tubing, tubing/frit, and silylated tubing/frit

| tubing | retention time (min) | peak height (mV) | peak bandwidth at half height (min) |
|---|---|---|---|
| silylated tubing/frit | 0.448 ± 0.037 | 7.771 ± 0.175 | 0.956 ± 0.051 |

(5 cm length, 0.1 mm I.D., 5 measurements each)

According to Table 1, silylated tubing/frit's show narrower bandwidths, higher peak heights, and short retention times when compared to different type tubings. We can know that not only the silanol groups of sintered silica but also the hydroxyl groups of stainless steel surface are quite deactivated by silylation based on the results of Table 1.

EXAMPLE 7

Production of Liquid Chromatography Microcolumn Installed with Stainless Steel Tubing/Frit's of Sintered Inorganic Oxide Powder Frits The following procedures are carried out to apply the above tubing/frit's to a microcolumn.

Figure 2A:
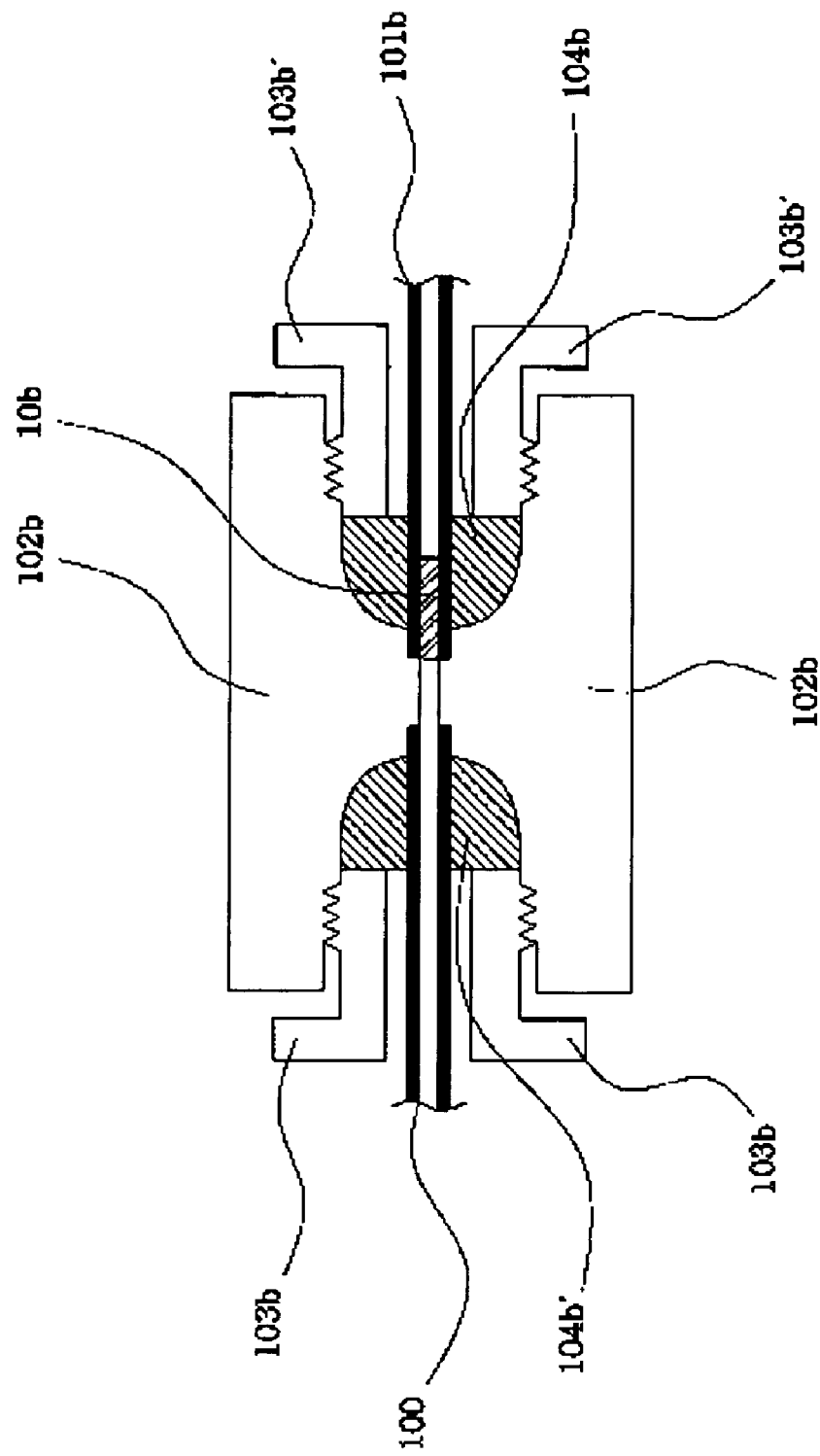
FIG. 2a is the enlarged drawing of the column outlet shown in FIG. 1.
Figure 2B:
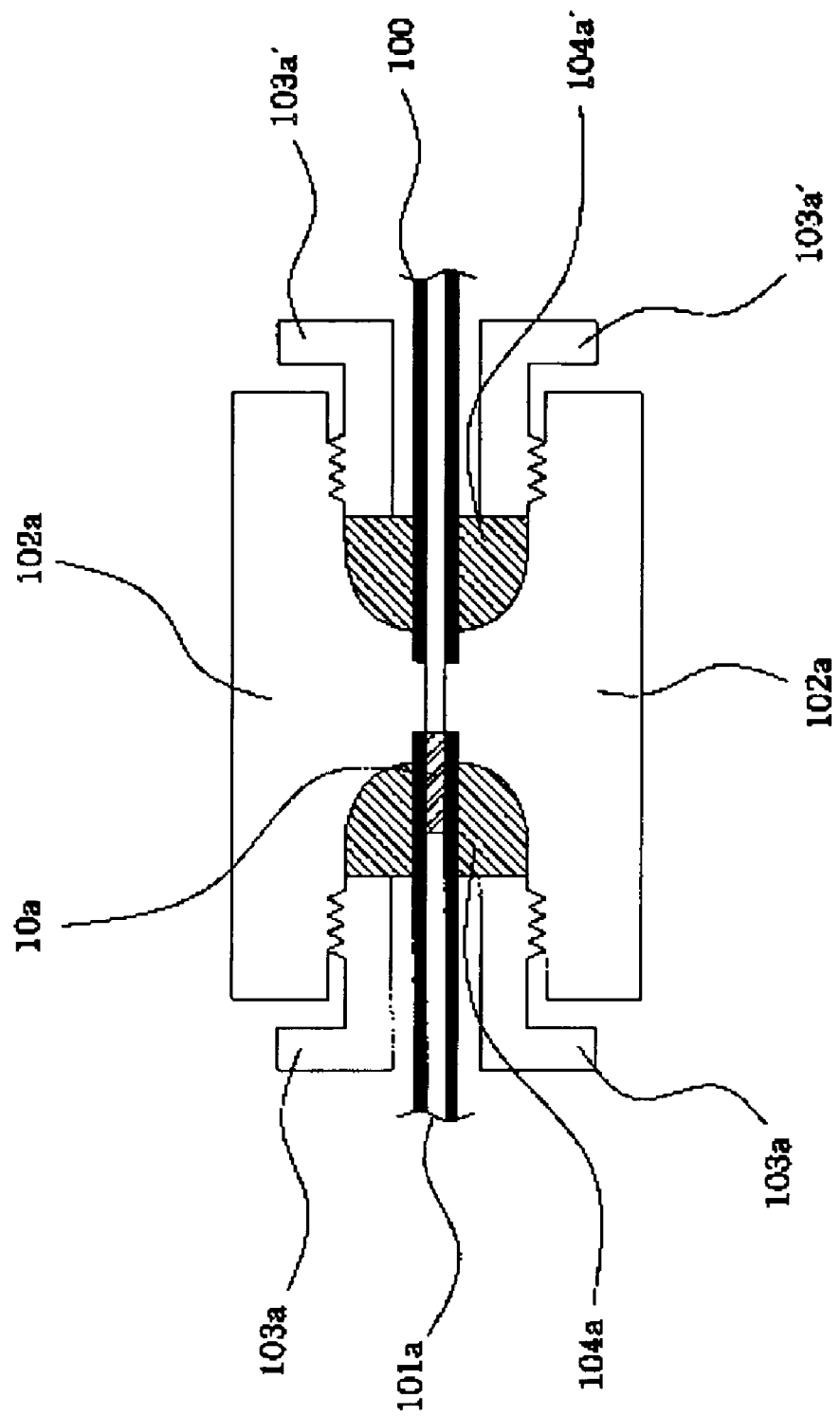
FIG. 2b is the enlarged drawing of the column inlet shown in FIG. 1.
Figure 3:
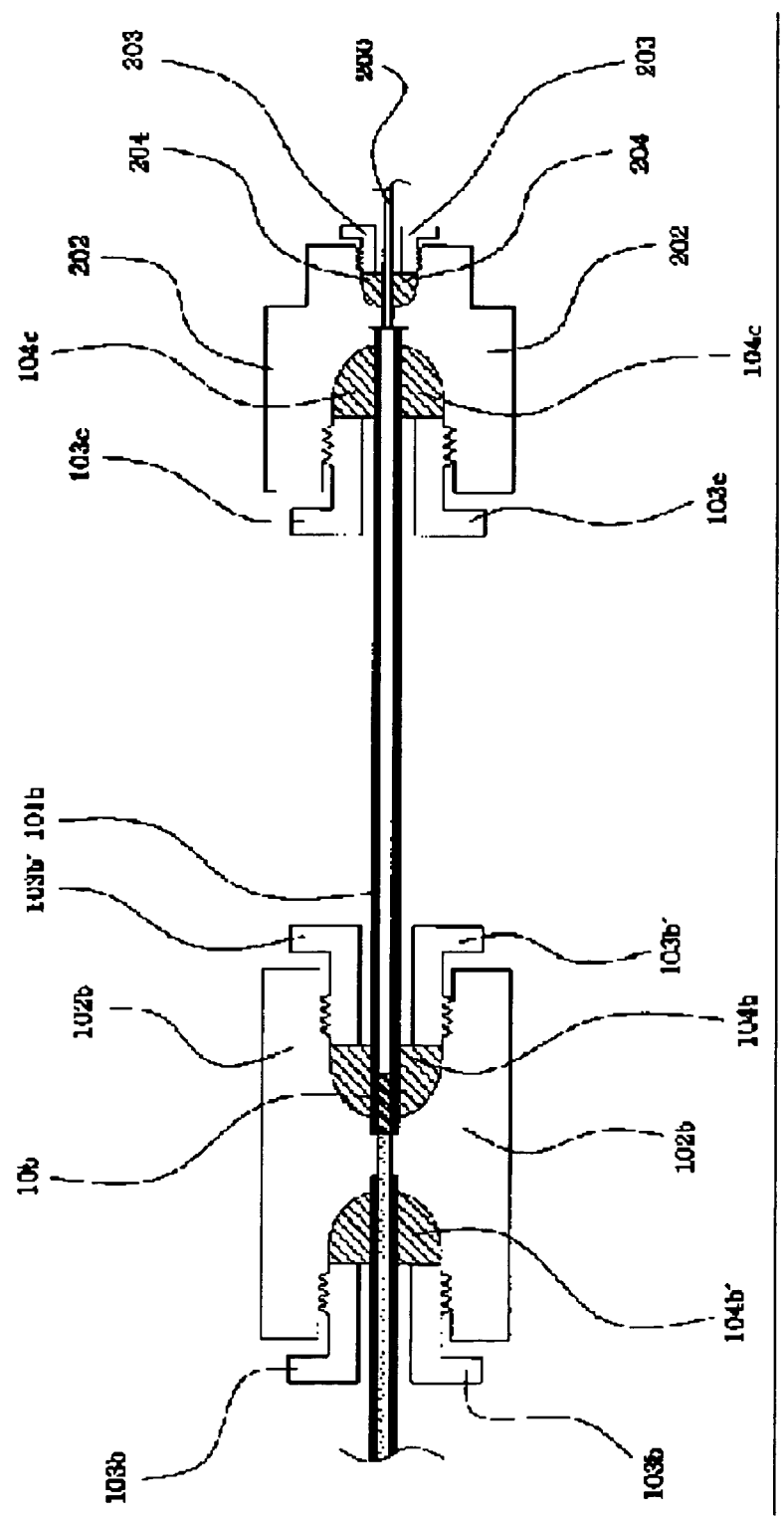
FIG. 3 is an illustrative drawing showing how to connect a chromatographic column to a mass spectrometer.

The stainless steel tubing/frit(101$b$, 5 cm length, 0.1 mm I.D., 1.6 mm O.D.) with the sintered powder frit(10$b$) is connected to the column outlet union with a nut(103$b'$) and a ferrule(104$b$) as shown in FIG. 2$a$.

The main body column tubing(100, glass-lined, 30 cm length, 0.5 mm I.D., 1.6 mm O.D.) to be packed with stationary phase powders is connected to the other side of the union, and the open end of the main body column tubing is connected to the column packing apparatus.

The Alltima $C_{18}$ stationary phase (5μ) of 200 mg is dispersed in 6 mL methanol, untrasonicated, and poured into a 4 mL slurry reservoir for immediate column packing. Packing is executed under a high pressure of 14,000 psi for 2 minutes, followed by conditioning under 8000 psi for 30 minutes.

After completion of packing, the main body column tubing(100) is detached and connected to the column inlet union(102$a$) with stainless steel tubing/frit(101$a$) as shown in FIG. 2$b$ to complete the column like one in FIG. 1.

Separation performance of the above microcolumn is examined for a test mixture. 90/10 (vol %) methanol/water mixed solvent is used as the eluent, and the Alltima $C_{18}$ column(I.D.×length: 0.5 mm×30 cm) packed with a 5μ stationary phase is used. The eluent flow rate is 10 μL/min, and the obtained chromatogram is shown in FIG. 6$a$.

Figure 6A:
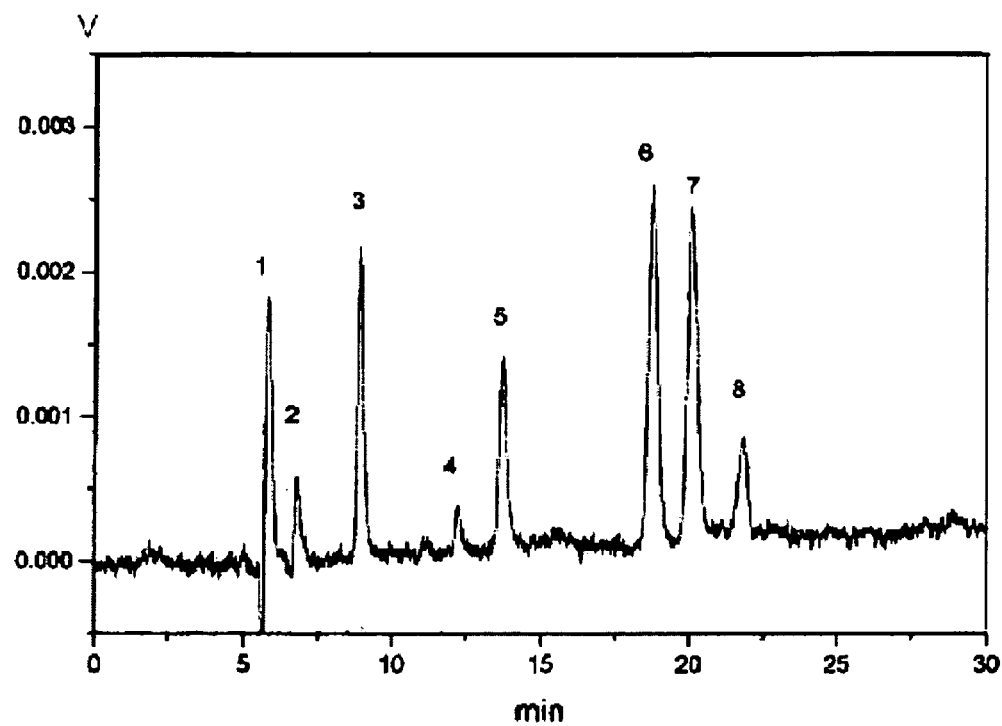
FIG. 6a and FIG. 6b are the chromatograms of peaks separated by the columns manufactured by this invention.
Figure 6B:
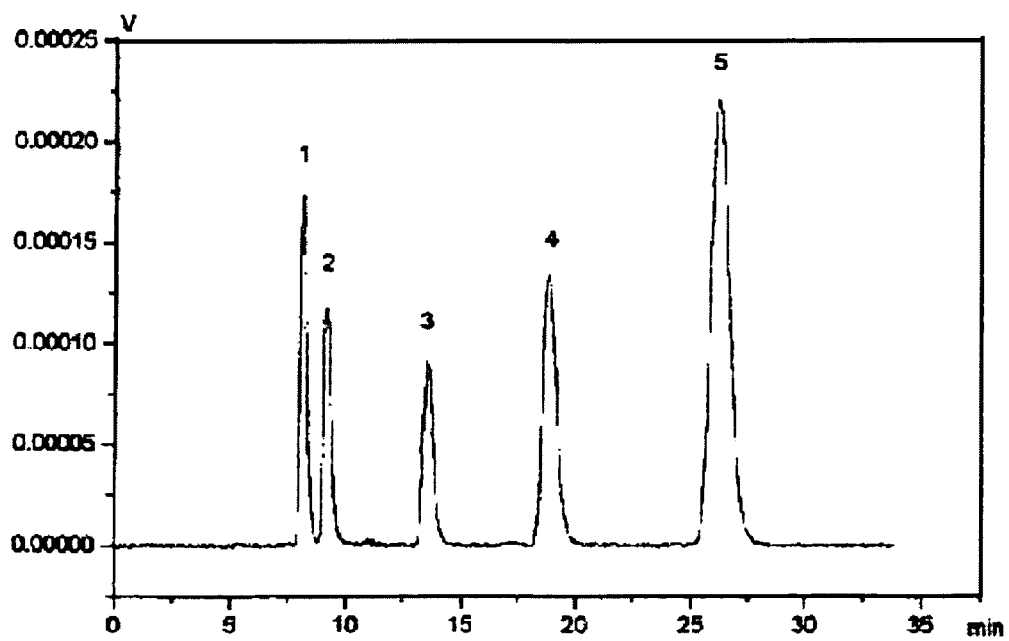

According to FIG. 6$a$, 1,4-methoxyphenol, acetophenone, ethylbenzoate, ethylbenzene, acenaphthylene, acenaphthene, phenanthrene, and anthracene in the test sample are separated in sequence, and good column efficiency is observed.

EXAMPLE 8

Liquid Chromatography—Mass Spectrometry System with the Microcolumn.

A mass spectrometer is coupled to the microcolumn produced in Example 7. A commercial asymmetric 1.6 mm/0.8 mm union(202) is connected to the microcolumn, and the ferrule of the 0.8 mm side is replaced by a commercial Vespel/graphite ferrule(0.4 mm I.D.), and a polymer coating reinforced silica capillary (O.D.×I.D.: 0.4 mm×0.05~0.1 mm) is cut in a proper length, and is connected therein.

EXAMPLE 9

Production of a Regular Liquid Chromatography Column Installed with Stainless Steel Tubing/Frit's of Sintered Inorganic Oxide Powder Frits.

The following procedures are carried out to apply the above tubing/frit to a regular column.

The stainless steel tubing/frit(101$b$, 5 cm length, 0.25 mm I.D., 1.6 mm O.D.) with the sintered powder frit(10$b$) is connected to the column outlet union(102$b$) with a nut (103$b'$) and a ferrule(104$b$) as shown in FIG. 2$a$.

The main body column tubing to be packed with stationary phase powders is connected to the other side of the union, and the other end of the main body column tubing is connected to the column packing apparatus. A stainless steel tubing (25 cm length, 4.6 mm I.D., 6.4 mm O.D.) with a ground inner wall of mirror-like surface is used as the main body column tubing.

A Kromasil $C_8$ (8μ) stationary phase of 2.5 g is dispersed in 25 mL methanol, unltrasonicated, and poured into a 20 mL slurry reservoir for immediate column packing. Packing is executed under a high pressure of 10,000 psi for 2 minutes, followed by conditioning under 8000 psi for 30 minutes.

After completion of packing, the main body column tubing(100) is detached and connected to the column inlet union(102$a$) with stainless steel tubing/frit(101$a$) as shown in FIG. 2$b$ to complete the column.

Separation performance of the above column is examined for a test mixture. 70/30 (vol %) methanol/water mixed solvent is used as the eluent, and the Kromasil $C_8$ column packed with a 8μ stationary phase is used. The eluent flow rate is 0.5 mL/min, and the obtained chromatogram is shown in FIG. 6$b$.

According to FIG. 6$b$, phenol, acetophenone, benzene, toluene, and ethylbenzeze in the test sample are separated in sequence, and satisfactory resolution is obtained.

INDUSTRIAL APPLICABILITY

Therefore, the inorganic oxide powder frit and tubing/frit are produced through chemical and thermal treatments in this invention. For the chromatography column made with such tubing/frit's, there is an advantage that only the connecting tubing is replaced without disassembling the column when replacement of the frit is necessary since the frit is installed in the connecting tubing unlike the conventional column where the frit is installed inside the column.

Especially, the tubing/frit of this invention is useful for a microcolumn with I.D. of 0.5 mm or less, since there is a critical disadvantage for the conventional microcolumn that the frit is permanently bound to the column end, thus the production is complicated and costly, and furthermore, the column lifetime is over because of impossibility of frit replacement when the frit is clogged, while the column of this invention, solves the problem, is capable of easy frit replacement and even of column disassembly for fix, and is a promising substitute as a new microcolumn.

The invention claimed is:

1. A chromatography column where specifically a tubing/frit with a sintered frit at a tip is connected to the outlet of the main body column tubing through connecting means, and the inlet of the main body column tubing is connected to another tubing/frit with a sintered frit at a tip also through connecting means, and the two sintered frits face each other with the main body column tubing between them.

2. The chromatography column of claim 1 where specifically the main body column tubing is made of material selected from the group consisting of stainless steel, nickel, and copper.

3. The chromatography column of claim 1 where specifically separate connecting elements are coupled to the open side of the tubing/frit bound to the outlet of the main body column tubing in order to offer connecting means to a separate detecting device.

4. The chromatography column of claim 1,
where the tubing/frit's with sintered frits are connected to the cylindrical main body column tubing packed with a stationary phase, respectively, and the components are combined by the common connecting means so that the frits at the column inlet and outlet face each other,
and the metal tubing/frit with the sintered frit is made from inorganic oxides treated with a strong base and dried to yield a product of some humidity and when the inorganic powders are filled at a proper height inside the tip of a metal tubing and is connected to the main body column tubing by installing the tubing/frit at the column outlet union, and the column outlet part is formed by installing it at the union with nuts and ferrules as connecting means, and the open side of the main body column tubing is connected to the column packing apparatus, and the main body column tubing is packed with a stationary phase, and the metal tubing/frit with a sintered frit is connected to the open side of the main body column tubing by installing it at the column inlet union, and the column inlet part is formed by using nuts and ferrules as connecting means.

* * * * *